United States Patent [19]
Patel

[11] Patent Number: 4,783,416
[45] Date of Patent: Nov. 8, 1988

[54] ANALYTICAL METHOD TO DETERMINE THE UNWASHED GUM CONTENT IN A GASOLINE BOILING HYDROCARBON

[75] Inventor: Jitendra G. Patel, Katy, Tex.

[73] Assignee: Shell Oil Company, Houston, Tex.

[21] Appl. No.: 47,951

[22] Filed: May 8, 1987

[51] Int. Cl.$^4$ .................. G01N 33/22; G01N 33/30
[52] U.S. Cl. ................................ 436/60; 436/140; 356/70
[58] Field of Search .................. 436/60, 139, 140; 250/373; 356/51, 70, 300; 208/255

[56] References Cited
U.S. PATENT DOCUMENTS

| | | | |
|---|---|---|---|
| 2,822,475 | 2/1958 | Miller | 250/43.5 |
| 2,847,578 | 8/1958 | Staten, Jr. | 250/43.5 |
| 2,900,510 | 8/1959 | Sparks, Jr. | 250/43.5 |
| 2,905,823 | 9/1959 | Sparks, Jr. | 250/43.5 |
| 4,149,805 | 4/1979 | Chew, III | 356/416 |
| 4,388,408 | 6/1983 | Sien et al. | 436/60 |
| 4,556,326 | 12/1985 | Kitchen, III et al. | 436/155 X |

OTHER PUBLICATIONS

Robinson, "Handbook of Spectroscopy", vol. II, CRC Press Inc., Boca Raton, Fla., pp. 133-181 and p. 214, 1981.

Primary Examiner—Michael S. Marcus
Assistant Examiner—Timothy M. McMahon
Attorney, Agent, or Firm—Kimbley L. Muller

[57] ABSTRACT

The invention disclosed is a method of determining gum content and performing quality control in the production of a gasoline to minimize the gum content in the produced gasoline. A representative sample of the gasoline is subjected to UV spectrophotometric analysis and the peak heights representing absorption in the range of 310 to 600 nm are integrated to determine a total absorption quantity which relates to the actual and potential quantity of gum in the gasoline. Use of this quality control technique will result in a refiner having more control over gum content at a hydrocarbon processing unit, such as a catalytic reformer.

5 Claims, 2 Drawing Sheets

SPECTROPHOTOMETRIC ANALYSIS OF A TYPICAL PERFORMANCE OR GASOLINE SAMPLE

ANALYTICAL METHOD TO DETERMINE THE UNWASHED GUM CONTENT IN A GASOLINE BOILING HYDROCARBON

FIELD OF THE INVENTION

The field of this invention relates to the quality control exercised upon the content of gasoline product to insure a minimum quantity or at least marketplace specification of gum components or gum precursor components. With the advent of fuel injectors in contemporary automobiles and trucks, the quality of gum in a gasoline boiling hydrocarbon has become more critical. In fact, gum can cause induction system deposits and sticking of intake valves. Low content of gum in gasoline is preferred but even minute particles of gum can partially or completely plug a fuel injector part thereby causing bad engine performance. Normally, an acceptable gum specification content in gasoline is the presence of less than 2 mg/100 ml. In furtherance of this target specification for low gum content a new, useful and very simple analytical control method has been developed to help control gum.

The widespread adoption of catalytic reforming to produce unleaded gasoline has resulted in smaller amounts of unstable hydrocarbons in the gasoline than were previously present with products derived by thermal cracking. These unstable and reactive hydrocarbons, although not technically gum but gum precursors, are present in the gasoline and subject to oxidation which then results in gum formation. And this situation is present regardless of whether or not the gasoline is sold immediately or is stored over a long storage time before sale and/or use. It is still accepted as necessary to include an antioxidant, i.e., a phenylenediamine or aminophenol, in the gasoline product.

Gum formation is generally a derivative of both olefin content and polynuclear aromatic content. Unwashed gum is comprised of long chain paraffins (waxes), oxidized conjugated dienes, polynuclear aromatics and their reaction products. Washed gum (after extraction with n-heptane) is comprised of mainly polynuclear aromatics and reaction products of the same. It is believed that the polynuclear aromatic content has a greater propensity to produce gum in finished gasoline than waxy long chain paraffins. Usually washed gum content follows unwashed gum content in quantity. This invention seeks to analyze for the quantity of polynuclear—aromatic and olefinic—gum precursor content. This technique will not have any effect upon other additives, such as anti-icing additives, lubricants, octane rating or volatility.

Currently the amount of gum present in a gasoline is determined by ASTM Test D-381. Washed gum is determined by evaporating a 50 ml sample to near dryness by a jet of heated air, washing the residue with a liquid hydrocarbon, such as normal heptane to remove any high boiling additives that may be present, and then weighing the washed residue of gummy material. The test for unwashed gum is determined in a like manner without washing the gummy residue with a normal hydrocarbon such as n-heptane. Both of these tests fail to indicate the content of gum precursors in manufactured gasoline, which during storage at a refinery or service station can develop into nefarious gum.

Another gum-stability test is ASTM D-873, which combines the air-jet gum test of ASTM D-381 with an oxidation stability test to determine potential residue in aviation gasolines. A 100 ml sample of fuel is exposed to oxygen in a heated vessel for a specified time and then evaporated to dryness by the air-jet method. The results are expressed in milligrams of gum per 100 ml. While these tests are accurate practical indicators of gum content, neither of these ASTM tests presents a quick and feasible analytical technique to determine the ultimate gum content in a gasoline. This invention seeks to provide an easy, economical, accurate and simple test to determine gum formation and content.

BACKGROUND OF THE INVENTION

The use of ultraviolet or UV-absorption for analyzing the contents of a petroleum distillate are well known. A method of testing and treating stored fuel was described in Kitchen, III et al, U.S. Pat. No. 4,556,326 issued Dec. 3, 1985. While it is not explicitly set forth that this testing method was to determine gum content in a distillate fuel, it would appear that gum content was at least a major concern. The analytical method utilizes UV absorption. A sample is acquired from a fuel tank and is heated to a high enough temperature below the boiling point of the fuel to accelerate the formation of macroscopic agglomerates by rapid polymerization of agglomerating agents. UV transmission characteristics of the fuel sample are acquired before heating, after heating and after cooling. The transmission characteristics are determined at a single wave length or a single narrow band of wave lengths between 400 and 680 nanometers. The most preferred single wave length is at 572 nanometers. In the quality control of a gasoline range distillate hydrocarbon, this type of testing procedure is not viable. In addition, it has been discovered, as shown in the instant drawings, that total absorption at 572 nanometers is not viable to determine gum content of a gasoline range distillate hydrocarbon. This test is also not viable as an on-line analytic test method for determining gum content in a gasoline boiling range hydrocarbon. In contrast, the instant invention is very simple yet accurate. It does not require testing of a preheated sample, a heated sample and then a cooled sample in order to adequately determine gum content.

Two ultraviolet analyzers for determining the content of butadiene in a hydrocarbon are disclosed in U.S. Pat. No. 2,847,578 issued Aug. 12, 1958 and U.S. Pat. No. 2,822,475 issued Feb. 4, 1958. The teachings of these analyzers are herein incorporated by reference as they relate to the ability of a UV analyzer to focus on a particular portion of a UV spectrum. Sparks,Jr., U.S. Pat. Nos. 2,900,510 and 2,905,823, also discloses analyzers for determining butadiene content. The disclosure of the analytical hardware tools of these two references is also incorporated by reference herein to this specification.

Slurry coker feedstock is analyzed in Sien et al, U.S. Pat. No. 4,388,408 issued June 14, 1983 to determine via UV absorptivity the suitability of the feedstock to produce electrode grade coke. This disclosure, like that of Kitchen et al, relies upon individual wavelengths and not on the integration or summation of a number of absorptions over a range of wavelengths. ASTM test methods D-2007 and D-2008 specify wavelengths characteristic of most polynuclear aromatics of between 280 and 400 millimicrons. Three specific wavelengths are noted. Tests 1 through 15 of Table 1 of the patent show representatives of these three peak heights. Finally, in Chew III, U.S. Pat. No. 4,149,805 issued Apr. 17, 1979, the amount of kerogen of an oil shale is taught as being proportional to the amount of light absorbed by the oil shale at a selected wavelength.

OBJECTS AND EMBODIMENTS

It is an object of this invention to provide an analytical method for feasible and reliable determination of gum content in a reformer effluent.

Another object of this invention is to provide a simple and economical analytical method by which to guarantee a minimal amount of gum content in a gasoline range distillate hydrocarbon. This will mitigate fuel injector clogging.

Another object of this invention is to provide a quality control means to indicate to a refiner the necessity to change or modify a feedstock material dependent upon a quick direct analysis of the effluent material.

One embodiment of this invention resides in a method of determining the potential gum content of a distillate hydrocarbon which comprises sampling said hydrocarbon and subjecting said sample of said hydrocarbon to UV spectrophotometric analysis and integrating peak absorptions in the range of from 310 to 600 nm.

Another embodiment of this invention resides in a method for the quality control of gasoline to minimize the gum content of manufactured gasoline, which comprises subjecting at least a sample of the gasoline to UV spectrophotometric analysis in the range of from 310 to 600 nm, summing the peak absorption heights present in that range and correlating that summation to a predetermined relationship to arrive at the estimated gum content in said gasoline.

Yet another embodiment of this invention resides in an analytical method to determine the actual and/or potential gum content in a hydrocarbon by means of spectrophotometric analysis which comprises integrating the peak absorption heights in the wavelength of from 310 to 600 nm and correlating that to a predetermined value representative of the actual gum content.

BRIEF DESCRIPTION OF THE INVENTION

This invention concerns a method to ensure quality control of gasoline, especially gasoline blended with reformate, to minimize the gum content. A significant relationship has been found to exist in the range of 310-400 nm UV spectrophotometric absorption representative of gum content in catalytic reformate. This invention can function as an online analyzer for an effluent stream derived from a catalytic reformer unit.

DETAILED DESCRIPTION OF INVENTION

This invention relates to a new analytical method to determine existent gum in hydrocarbon fuels in a more reliable manner than current ASTM Test D-381. A correlation has been achieved between a relatively narrow spectrum of the total absorbtion of dienic and polynuclear aromatic compounds.

As demonstrated in the following illustrative embodiments, this invention method of analysis has a greater reliability of duplication than the current ASTM testing methods. Surprisingly, this correlation of this specific spectrum of integrated wavelength has been found to be representative of unwashed gums but surprisingly not necessarily correlative to washed gums. This analytical method was performed on reformates taken from a catalytic reforming unit. While gasoline is a blend of different reformates and other hydrocarbons, it is believed that if the gum content of the reformate can be controlled, then the gum content of ultimate retail gasoline at pumps may be assumed to be at controlled gum levels. Also, gum level in the final blended gasoline stock can be further controlled by blending gasoline streams of only certain known gum content. In this manner, the ultimate gum level in the blended gasoline can be precalculated by a blender.

This analytical method involves the use of UV/Visible spectrophotometric analysis. This analysis may be made on any conventional spectrophotometer as exemplified by the above cited, and incorporated by reference, patents, and by current spectrophotometers such as Bausch and Lomb UV Spectrometer (Spectronic 20), Perkin-Elmer Lambda Spectrophotometers, (Series 4B, 5, 7 and 9), IBM Spectrophotometer 9420, Beckman Spectrophotometer DU7, Varian Spectrophotometer DMS200, etc. It is preferred that these samples be run against a solvent cell filled with clean, known solvent of particular known wavelength adsorption e.g. n-heptane. However, this analytical method can develop its baseline utilizing air as the second cell solvent. It is not critical which type of baseline cell is utilized as long as a known constant baseline is established for both the correlation and the analysis of the results.

The UV/Visible absorption of a hydrocarbon is strongly affected by dienes and polynuclear aromatics but very little by paraffins. As a result it has been determined that a very large peak height exists in the UV spectrum at a point beginning well before 300 nms and continuing to 400 nms. In operation, the analytical chemist will sample reformate to determine its polynuclear content and diene content, and run a spectrum in order to attenuate a peak at no greater than 2.0 Absorption Units (AU). If a relative increased quantity of these materials is present, and a peak height greater than 2.0 AU exists, it then becomes necessary to run a sample diluted by a certain amount of known solvent and obtain a second or third spectrum of peak heights ranging from 310-600 nm. This invention is significant in that applicants have determined a very narrow integrated range of the spectrum, i.e., 310-400, which is representative of unwashed gum content. Integration acts as a smoothing function in the interpretation of data to eliminate "noise" at individual wavelengths, which may give erroneous interpretation of the quantity of certain components. While this relationship is not necessarily commensurate with washed gum, it is observed that if the unwashed gum is found to be excessive, then washed gum level is usually expected to be high. Conversely, it can also be said that if unwashed gum is found to be missing or low then the washed gum level is expected to be low.

In this method of analysis, the absorptions determined in a UV/Visible light spectra greater than 310 nm are integrated to determine the unwashed gum content. The measured light spectrum less than 310 nm is irrelevant to this determination. The test method will normally determine a spectrum up to 600 nm in order to detect any possible abnormality in the test sample. It is necessary that all work be performed between 310 and 600 nm for an accurate test but that normally no absorbance is measured between 400 and 600 nm.

The advantages of this spectrophotometric method is that it provides a simple means in which elaborate sample preparation (i.e., heating and cooling) is eliminated to determine actual gum content. Elaborate cleaning, adjustment of equipment and measurements are not necessary to insure accurate reproducibility of results.

The results can be generated in a matter of a few minutes. This method is useful for on-line use and quality control. Another advantage is that the instant test is sensitive to small changes in gum content which will allow for better precision and reproducibility in results. Also, once a refiner is notified of a potential high gum content by this test (i.e., the quantity of unwashed gum is increasing), positive steps can be taken in preparation and treatment of the feed material to mitigate unwashed gum content in the reformate. The achievement of the correlation of this particular spectrum to this technique is established by the data of the following illustrative embodiments which are exemplified by FIGS. 1 and 2.

ILLUSTRATIVE EMBODIMENT

Figure 1:
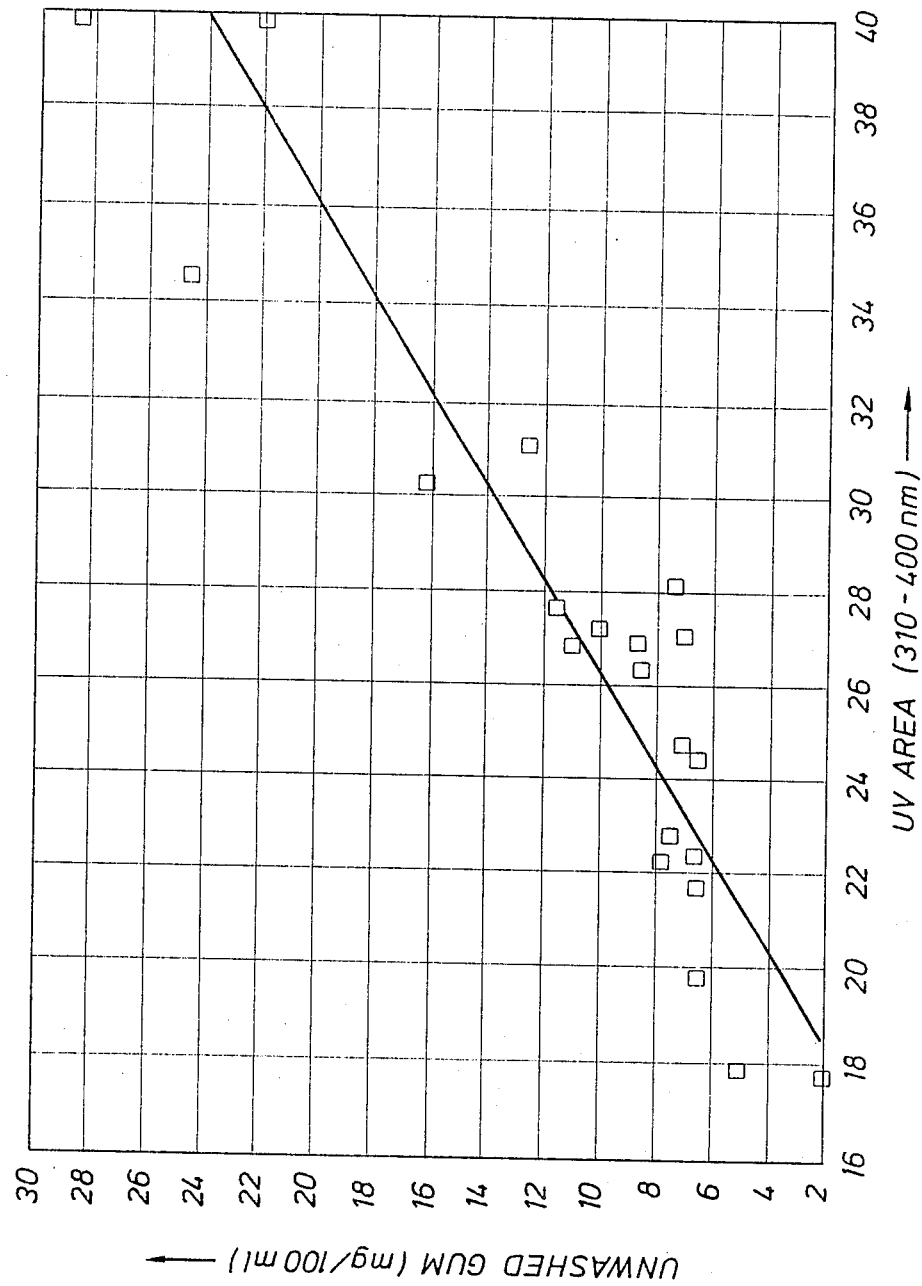
FIG. 1 is a demonstration of the linear relationship of peak integration versus actual gum content on a number of duplicate samples.

In order to demonstrate the analytical relationship of spectrum area to gum content, various reformates from a commercial catalytic reforming unit were analyzed by two different analytical methods. First, ASTM D-381-80 was utilized to determine unwashed gum content. This method was also retested to determine its reproducibility. The same reformate samples were subjected to UV/Visible analysis by the following procedure. A Perkin-Elmer Lambda 7 UV Visible Spectrophotometer was utilized with a Perkin-Elmer 750 Data Processing station in order to integrate desired peak heights. Initially, the instrument was calibrated and a baseline was established. The sample used to establish the baseline was n-heptane. Each sample of the reformate was placed in a clean, transparent cell and placed in the sample compartment. A spectrum of the sample was analyzed neat from 280–600 nm. The spectrum for wavelengths past 400 nm was obtained only to insure the spectral uniformity in the aromatic absorption region. The samples were run so that the absorbance at 300 nm did not exceed (2.0) two absorption units. After the sample spectrum was achieved, a subtraction was made for the baseline of the UV analyzer, and a Perkin-Elmer integrator was used to complete integration of all the absorbance peak heights between 310–400 nm. In order to determine the reproducibility of this analytical method., each sample was run twice. Table 1 sets forth all of these tests results.

TABLE 1

| A<br>Area<br>#1 | B<br>Area<br>#2 | C<br>Ave.<br>Area | D<br>Ungum<br>#1 | E<br>Ungum<br>#2 | F<br>Ungum<br>Ave. | G<br>Wgum<br>#1 | H<br>Wgum<br>#2 | I<br>Wgum<br>Ave. | J<br>% Diff. from Average UV | K<br>% Diff. from Average Gum |
|---|---|---|---|---|---|---|---|---|---|---|
| 17.69 | 17.69 | 17.69 | 2.0 | 2.0 | 2.0 | 1.0 | 1.0 | 1.0 | 0.06 | 0.00 |
| 17.76 | 17.81 | 17.79 | 5.0 | 5.0 | 5.0 | 1.0 | 1.0 | 1.0 | −0.28 | 0.00 |
| 19.71 | 19.71 | 19.71 | 7.0 | 6.0 | 6.5 | 2.0 | 2.0 | 2.0 | 0.00 | 15.38 |
| 21.51 | 21.76 | 21.63 | 6.4 | 6.6 | 6.5 | 2.6 | 3.0 | 2.8 | −1.16 | −3.08 |
| 22.12 | 22.54 | 22.33 | 6.0 | 7.2 | 6.6 | 4.2 | 5.0 | 4.6 | −1.88 | −18.18 |
| 22.66 | 22.88 | 22.77 | 8.0 | 7.0 | 7.5 | 7.0 | 5.0 | 6.0 | −0.97 | 13.33 |
| 24.40 | 24.36 | 24.38 | 6.0 | 7.0 | 6.5 | 2.0 | 3.0 | 2.5 | 0.16 | −15.38 |
| 25.11 | 24.26 | 24.69 | 7.0 | 7.0 | 7.0 | 4.0 | 3.0 | 3.5 | 3.44 | 0.00 |
| 26.34 | 26.32 | 26.33 | 8.0 | 9.0 | 8.5 | 2.0 | 2.0 | 2.0 | 0.08 | −11.76 |
| 26.85 | 26.77 | 26.81 | 10.0 | 12.0 | 11.0 | 4.0 | 5.0 | 4.5 | 0.30 | −18.18 |
| 26.89 | 26.92 | 26.91 | 9.2 | 8.0 | 8.6 | 1.6 | 1.8 | 1.7 | −0.11 | 13.95 |
| 27.20 | 27.20 | 27.20 | 11.0 | 9.0 | 10.0 | 5.0 | 4.0 | 4.5 | 0.00 | 20.00 |
| 27.60 | 27.70 | 26.65 | 11.0 | 12.0 | 11.5 | 5.0 | 6.0 | 5.5 | −0.36 | −8.70 |
| 31.11 | 31.06 | 31.09 | 13.0 | 12.0 | 12.5 | 4.0 | 2.0 | 3.0 | 0.16 | 8.00 |
| 30.08 | 30.43 | 30.23 | 17.0 | 15.4 | 16.2 | 4.8 | 3.2 | 4.0 | −1.16 | 9.88 |
| 33.98 | 35.05 | 34.52 | 26.0 | 23.2 | 24.6 | 4.4 | 2.8 | 3.6 | −3.10 | 11.38 |
| 39.70 | 39.75 | 39.73 | 32.0 | 25.0 | 28.5 | 8.0 | 12.0 | 10.0 | −0.13 | 24.56 |
| 39.67 | 39.98 | 39.83 | 23.0 | 21.0 | 22.0 | 7.0 | 4.0 | 5.5 | −0.78 | 9.09 |
| 22.20 |  | 22.20 | 8.0 | 7.6 | 7.8 | 2.4 | 3.0 | 2.7 | 0.00 | 5.13 |
| 27.09 |  | 27.09 | 7.0 | 7.0 | 7.0 | 2.0 | 3.0 | 2.5 | 0.00 | 0.00 |
| 28.16 |  | 28.16 | 7.8 | 7.0 | 7.4 | 3.6 | 3.8 | 3.7 | 0.00 | 10.81 |

Columns A and B are representative of the UV spectrophotometric absorbance area achieved between 310 and 400 nm. Column C is the average of these two tests. Column J demonstrates the percent difference of the two UV analyses based on the average value in Column C. Columns D and E are the representative of the tests run according to ASTM D-381-80. Column F indicates the average of those two test results. Column K indicates the variance in duplicating the test. A comparison of columns J and K clearly show that this analytical method is much more reliable (i.e., has a lack of variance) than ASTM Test D-381-80. Columns G and H are representative runs of ASTM Test D-381 wherein washed gum was analyzed. Column I is the average of those two tests. It can be seen from a comparison of Columns A-C versus Columns D-F, preferably Columns C and F, that there is a correlationship between the UV absorbance at 310–400 nm and actual gum content. These data points (Columns C and F) have been plotted as FIG. 1 to show the linear relationship of the peak height integration versus actual gum content. The absorbance determined by this test method can be empirically correlated by an actual graph or chart to actual gum content. The relationship of gum content to integrated absorbance does not have to be linear within the confines of this invention. Some trial and error commensurate with former ASTM tests may have to be completed but the actual gum content relationship by this method will readily be apparent to one of reasonable skill in the art. Once established by the applicable technique and the species of the instrument of analysis, the relationship will be continuing and correlation to actual gum content will readily be ascertainable to one of even modicum skill in this art. It is not possible to set forth the actual relationship of gum content vs. absorbance for every set of test parameters and instruments.

It is interesting to note that a comparison of columns A-C with Columns G-I do not show an accurate correlation of this spectrum with washed gum content. This is not yet fully understood at this time. However, if the unwashed gum content is reduced, then a reduction in washed gum content will follow.

Figure 2:
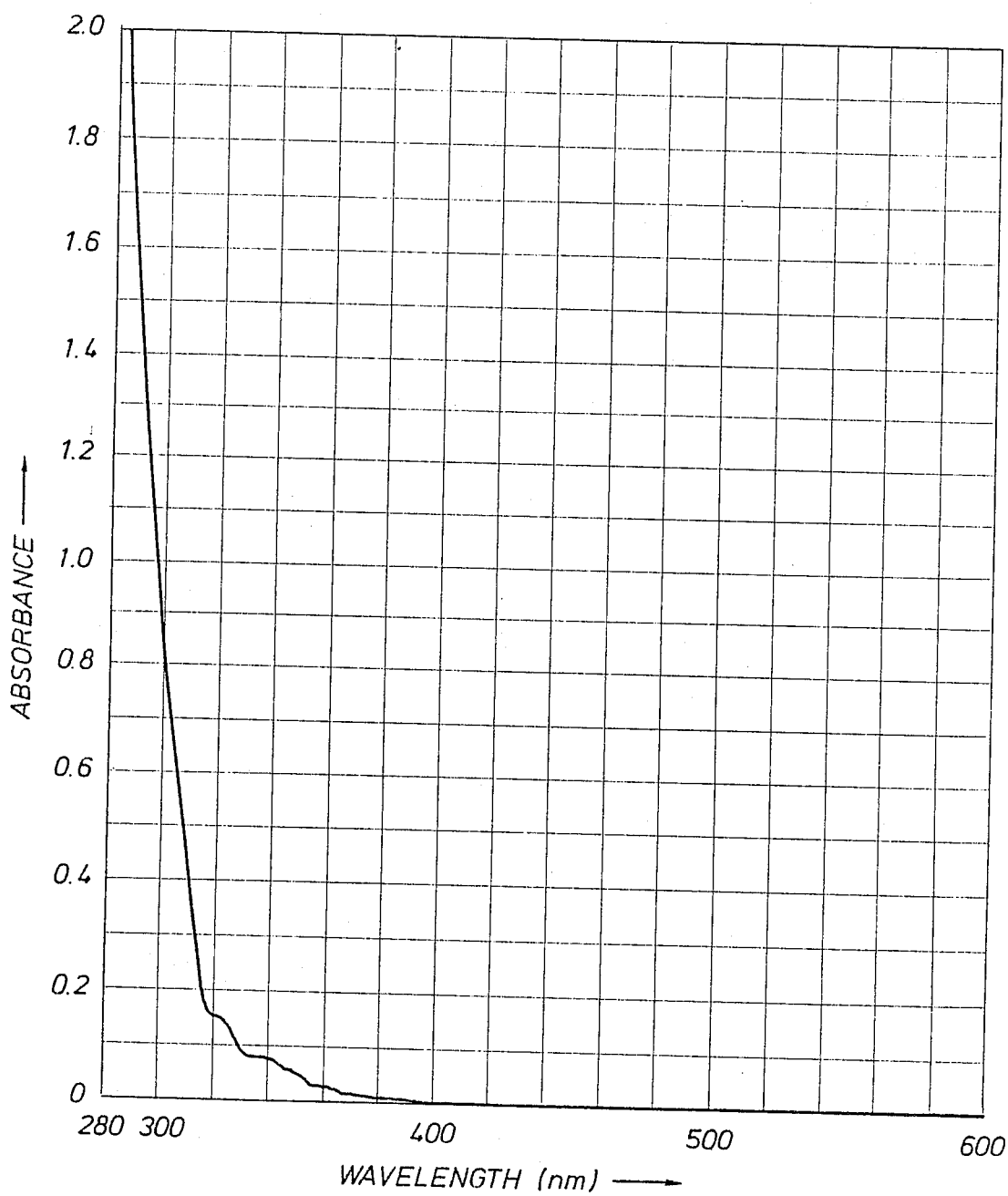
FIG. 2 is representative of a typical UV spectrum and the exact area in which integration of the absorbance is determined to attain a number which correlates to the actual gum content.

A representative of these spectrums is shown in FIG. 2 which demonstrates the type of absorbance necessary to determine this relationship. The total peak height between 280-400 is representative of different compounds previously thought to contribute to gum content. Only a small portion of the spectrum of adsorbance need to integrated, i.e., 310-400, which gives an accurate analysis of actual gum content.

What I claim as my invention is:

1. A method of determining the potential unwashed gum content of a distillate hydrocarbon which comprises sampling said hydrocarbon and subjecting said sample of said hydrocarbon to UV spectrophotometric analysis and integrating peak absorptions in the range of from 310 to 400 nm and thereby attaining a peak absorption area and comparing said peak absorption area to a predetermined standard, thereby attaining said unwashed gum content.

2. The method of claim 1 wherein said distillate hydrocarbon comprises the effluent from a catalytic reforming unit.

3. The method of claim 1 wherein said integration comprises summation of all peak heights within the range of 310 to 400 nm.

4. The method of claim 1 wherein said peak absorptions are representative of the content of at least a portion of polynuclear aromatic molecules in said hydrocarbon.

5. A method for the determination of unwashed gum content in a gasoline which comprises subjecting at least a portion of said gasoline to UV spectrophotometric analysis to attain peak absorption heights in the range of from 310 to 400 nm, and summing said peak absorption heights to attain a peak absorption area and comparing said peak absorption area to a predetermined standard to arrive at the unwashed gum content in said gasoline.

* * * * *